(12) United States Patent
Kim et al.

(10) Patent No.: US 7,846,484 B2
(45) Date of Patent: Dec. 7, 2010

(54) **COMPOSITION COMPRISING *HOVENIA DULCIS* THUNB. EXTRACT, *LINDERA OBTUSILOBA* BLUME EXTRACT, OR HERBAL MIXTURE EXTRACT THEREOF**

(75) Inventors: Kiyoung Kim, #104-904 DongA Apt., Busong-dong, Iksan, Jeollabuk-do (KR) 570-360; Kwangsang Kim, Jeollanamdo (KR)

(73) Assignees: Kiyoung Kim, Iksan (KR); Jangheunggun Mushroom Research Institute, Jeollanamdo (KR)

( * ) Notice: Subject to any disclaimer, the term of this patent is extended or adjusted under 35 U.S.C. 154(b) by 0 days.

(21) Appl. No.: 12/465,830

(22) Filed: May 14, 2009

(65) Prior Publication Data

US 2009/0285914 A1    Nov. 19, 2009

Related U.S. Application Data

(63) Continuation of application No. 10/587,286, filed as application No. PCT/KR2005/000283 on Jan. 31, 2005, now abandoned.

(30) Foreign Application Priority Data

| Jan. 31, 2004 | (KR) | 10-2004-0006435 |
| Jan. 31, 2004 | (KR) | 10-2004-0006436 |
| Jan. 31, 2004 | (KR) | 10-2004-0006437 |

(51) Int. Cl.
*A61K 36/00* (2006.01)

(52) U.S. Cl. ................ 424/779; 424/777

(58) Field of Classification Search ............ None
See application file for complete search history.

(56) References Cited

U.S. PATENT DOCUMENTS 5,879,709 A * 3/1999 Soon-Shiong et al. ....... 424/484

2004/0058016 A1 * 3/2004 Na et al. ................ 424/725

FOREIGN PATENT DOCUMENTS

| JP | 2003128571 | * 5/2003 |
| KR | 100214801 | 5/1999 |
| KR | 100076980 | 10/2002 |
| KR | 100403722 | 10/2003 |
| KR | 100543082 | 1/2006 |
| WO | WO 02/060463 | 8/2002 |
| WO | WO 03/059369 | 7/2003 |

OTHER PUBLICATIONS

Cho, J-Y et al., "Isolation and Identification of 3-Methoxy-4-hydroxybenzoic Acid and 3-Methoxy-4-hydroxycinnamic Acid from Hot Water Extracts of *Hovenia dulcis* Thunb and Confirmation of Their Antioxidative and Antimicrobial Activity," Korean J. Food Sci. Technol. 32(6):1403-1408, 2000, Abstract only.

Hase, K. et al., "Hepatoprotective effect of *Hovenia dulcis*THUNB. on experimental liver injuries induced by the carbon tetrachloride or D-galactosamine/lipopolysaccharide," Biol. Pharm. Bull. Apr. 20(4):381-385, 1997, Abstract only.

Yoshikawa, M. et al., "Bioactive constitutents of Chinese natural medicines. III. Absolute stereostructures of new dihydroflavonols, hovenitins I, II, and III, isolated from hoveniae semen seu fructus, the seed and fruit of *Hovenia dulcis* Thunb. (Rhamnaceae); inhibitory effect on alcohol-induced muscular relaxation and hepatoprotective activitry," Yakugaku Zasshi Feb. 117(2):108-118, 1997, Abstract only.

* cited by examiner

*Primary Examiner*—Christopher R. Tate
*Assistant Examiner*—Deborah A. Davis
(74) *Attorney, Agent, or Firm*—Greenlee Sullivan P.C.

(57) ABSTRACT

The present invention relates to a method for treating or preventing fibrosis and improving kidney function comprising administering a *Hovenia dulcis* Thunb extract and/or a *Lindera obtusiloba* extract to the subject. The method of the present invention can lower the level of GOT, GPT, ALP, BUN and total bilirubin; improve kidney functions; lower the amount of hydroxyproline in liver but increase the amount of hydroxyproline in kidney, suggesting that the extract above has excellent anti-fibrosis and kidney protecting effects; lower the level of malondialdehyde, suggesting that the extract has excellent anti-oxidative effect; and promote cell viability in liver and kidney cell lines, indicating that the extract has excellent liver and kidney cell protective effects.

2 Claims, No Drawings

US 7,846,484 B2

COMPOSITION COMPRISING *HOVENIA DULCIS* THUNB. EXTRACT, *LINDERA OBTUSILOBA* BLUME EXTRACT, OR HERBAL MIXTURE EXTRACT THEREOF

CROSS REFERENCE TO RELATED APPLICATIONS

This application is a continuation of U.S. patent application Ser. No. 10/587,286, filed Jul. 25, 2006, which is the National Stage Application of PCT International Application No. PCT/KR2005/000283 filed on Jan. 31, 2005, which claims benefit of Korean Patent Application Nos. 10-2004-0006435, 10-2004-0006436, and 10-2004-0006437, all of which were filed on Jan. 31, 2004, all of which are incorporated herein by reference in their entirety.

DESCRIPTION

1. Technical Field

The present invention relates to a composition comprising *Hovenia dulcis* Thunb extract, *Lindera obtusiloba* extract or herbal mixture extract thereof as an effective ingredient.

2. Background Art

As one of representative adult diseases, liver disease is caused by liver damage resulted from chronic fatigue by stress and most of exogeneous substances. The development rate of liver disease in Korea is very high, comparing to foreign countries, and in particular, the death rate of liver cancer is the top in the world and the death rate of chronic liver disease is the third. According to a recent report from National Statistical Office, Korea, liver disease is the leading cause of death of adults at the age of 40s in Korea. Among many liver diseases, the most fatal disease is viral hepatitis in Korea. In the meantime, the death by liver cirrhosis is 5~10 fold higher than that by viral hepatitis in Western countries.

Liver is the organ that shows the most active metabolism among many human organs. Acute or chronic damage in liver by in variety of reasons such as fatty diet, heavy drinking of alcohol, virus infection, poisons including chemicals, mal-nutrition, etc, might be developed into serious conditions like fatty liver, hepatitis, jaundice, hepatic cirrhosis and liver cancer. Particularly, fatty diet and heavy drinking of alcohol cause fatty liver, that is, lipid is accumulated in liver tissues. At this time, GOT (glutamate-oxaloacetate transaminase), GPT (glutamate-pyruvate transaminase) and γ-GTP (γ-glutamyl transpeptidase) increase in serum. Since liver has great buffer capacity, liver disease hardly shows symptoms in early stage, and only when it gets serious, it shows symptoms.

Liver has functions of preservation and circulation of blood, regulation of blood flow and detoxification, and is also known to be involved in mental activity. Human bodies are exposed on pollutions and lots of poison according to industrialization, so that the liver has to overwork in order to counteract poison. Liver damage by mental stress is worse. If human mind gets rest, damaged liver cells are recovered. The thing is that there is no extra time for rest for modern citizens. So, excessive mental stress, heavy smoke and alcohol drinking make liver damage worse, resulting in mal-function of detoxification, that is mal-function of immune system, which might be a cause of another disease.

Liver cirrhosis is caused by fibrosis of liver tissues, which is the condition of losing homeostasis between generation and degeneration of connective tissue. That is, connective tissue is over-accumulated in liver tissues, accompanying necrosis or inflammation. Fibrosis of liver tissues is progressed by the excessive generation of connective tissue resulted from the growth and transfer of hepatic stellate cells (HSCs) transformed in the form of myofibroblasts (Gressner et al., *Biochem. Biophys. Res. Commun.* 151~222, 1988). Liver cirrhosis is the final stage of every chronic liver diseases, by which liver loses its general functions rapidly with showing the decrease of hepatic blood flow, the reduction of blood flow in liver, mal-function of metabolizing enzyme, qualitative and quantitative changes in blood protein, variation of bile flux, etc.

Hepatotoxicity inducers are exemplified by carbon tetrachloride ($CCl_4$), D-galactosamine, lipopolysaccharide (LPS) and bromobenzene, and in particular, carbon tetrachloride is known to induce hepatotoxicity by inducting lipid peroxidation of liver cells (Recknagel et al., *Pharmacol. Rev.* 19:145-208, 1967; Alpers et al., *Mol. Pharmacol.* 4:566-573, 1968; Slater T. F., Biochem. J. 222: 1~15, 1994). Carbon tetrachloride is a hepatotoxicity inducer that has been used to investigate anti-hepatotoxic activity. Precisely, it has been administered to mice or rats, cultured liver cells and cultured liver tissues to induce hepatotoxicity artificially. Carbon tetrachloride is converted into the highly reactive molecular structure of free radical $CCl_3 \cdot$ in endoplasmic reticulum by metabolizing enzyme like cytochrome P450, by which it acquires a very strong hepatotoxic effect. Free radical $CCl_3 \cdot$ oxidizes triglyceride accumulated in liver by alcohol and fatty acid on membrane phospholipid, leading to acidification and oxidation of lipid, followed by lipid peroxidation. As a result, organic peroxide is produced. Through such lipid peroxidation, fat is accumulated in liver, protein synthesis is reduced, glycogen is decomposed, and cytoplasmic enzymes in blood vessel are destroyed, resulting in necrosis of liver tissues (Chang I. M., et al., *Drug and chemical toxicology* 6, 443-453, 1983). Free radical also harms Golgi apparatus, so that protein release out of cells is affected, suggesting that not only liver but also kidney might be damaged.

Anti-oxidation not only inhibits or prevents lipid peroxidation but also has liver protective and anti-inflammatory effects. Thus, an antioxidant compound has been used for the protection of liver and liver cells against attacks by reactive oxygen intermediate.

Antioxidant agents separated from natural resources such as flavonoid, quercetin, silymarin or vitamin E have been reported to have positive effect on lipid peroxidation and hepatic fibrosis. And, N-acetylcysteine (NAC) has been confirmed to reduce oxidative stress and hepatic fibrosis in the early stage of hepatic fibrosis by its anti-oxidative activity. *Picrorhiza Kurroa* (kutkin) is another natural anti-oxidative compound that has liver protective and anti-fibrosis effects by reducing damage caused by lipid peroxidation and free radical.

As of today, the treatment methods for liver diseases are largely divided into two ways; one is a dietetic therapy and the other is medicinal therapy. In most cases, the two methods are used together. For medicinal therapy, in variety of medicines having different functions are used according to the cause and type of liver disease. For example, liver cell reproduction stimulator and/or liver function protector such as ursodeoxycholic acid, silymarin (*Biotech. Therapeutics*, 4, 263-270, 1993), DDB (biphenyl dimethyl dicarboxylate; *Biochem. Biophy. Res. Comm.*, 103, 1131-1137, 1981), glutathione, glycyrrhizin, etc, antiviral agent such as acyclovir, and immunosuppressive drug such as corticosteroid, 6-mercaptopurine (6-MP), azathioprine, etc, are in use. However, liver disease is developed not by just one reason but by co-work of many factors. Thus, one medicine having a certain function is not enough for the treatment of every kinds of liver disease. The conventional medicine for the treatment of liver diseases has problems of unexpected reaction and other side effects by long-term or mass administration.

In the meantime, kidney has functions of regulating the concentrations of ion and body fluids, urinating waste products (urea, uric acid, creatinine, etc) and eliminating toxic substances, drugs and metabolites out of the system after counteracting poison. Malonedialdehyde (MDA) and 4-hydroxynonenal (HNE), products from lipid peroxidation in tissues, have been known as indices for cell damage. And, superoxide dismutase catalizing lipid peroxidation has been known to be involved in recovery from cell damage (Slater T F. Biochem. J., 222, 1-15, 1994; Esterbauer H, Schauer R J, Zollner H., 1994; Free Radical Biology & Medicine 11, 81-128, 1992). Besides, alkaline phosphatase (ALP) and blood urea nitrogen (BUN) are also in use as diagnostic indices for kidney functions. In particular, the increase of BUN indicates the decrease of glomerular filtration rate (GFR) by azotemia. Prerenal azotemia means kidney malfunction without kidney damage, which is resulted from hypoperfusion by congestive heart failure, shock, hypovolemia and hemorrhage. On the other hand, postrenal azotemia is caused when the flow of urin is blocked in the lower part of kidney. In the case of postrenal azotemia, full recovery is expected by the elimination of the cause. When azotemia accompanies various clinical symptoms and biochemical disorders, it is called uremia. Thus, uremia is not only a simple biochemical disorder but also a syndrome carrying metabolic disorders, endocrine disorders, gastrointestinal disorders, neuromuscular disorders and cardiovascular disorders, in addition to elimination disorders. Diseases caused by mal-function of kidney are exemplified by acute pyelonephritis, chronic pyelonephritis, renal tuberculosis, UTI, urinary stone, renal cell cancer, etc.

*Hovenia dulcis* Thunb. is a kind of deciduous broad-leaved tall tree belonging to Rhamnaceae, which is also called 'Jigumok' in Chinese medicine. There is an explanation on *Hovenia dulcis* Thunb. in Bon-cho-kang-mok that it tastes sweet and plain, has no toxicity, makes the five viscera (heart, liver, spleen, lungs and kidneys) work smooth and easy, eliminates fever in the chest, quenches thirst, neutralizes alcohol poisoning, relieves vomiting, detoxificates insect poison and might treat five types of hemorrhoids. It has also been known to have liver protective effect. Precisely, it has excellent activities of eliminating halitosis, improving alcoholic hepatitis, fatty liver and liver cirrhosis, anticancer, regulating blood pressure, lowering blood glucose, liver detoxication, and mitigating constipation.

*Lindera obtusiloba* is a kind of deciduous broad-leaved tall tree belonging to Lauraceae, which is distributed widely in Korea, Japan, China and Manchuria. The flowers, leaves and stems of *Lindera obtusiloba* emit unique fragrance. The stems of it have been used for medicinal purposes, owing to their anti-bacterial effect. Fresh shoots of it have been used for tea.

After long search of natural medicinal compounds having various working mechanisms with low toxicity, the present inventors have completed this invention by confirming that *Hovenia dulcis* Thunb extract, *Lindera obtusiloba* extract or herbal mixture extract thereof has activities of antioxidative, anti-fibrosis and improving liver functions, in addition to activities of protecting and improving kidney functions.

DISCLOSURE

Technical Solution

It is an object of the present invention to provide a composition comprising *Hovenia dulcis* Thunb extract, *Lindera obtusiloba* extract or herbal mixture extract thereof as an effective ingredient.

Best Mode

The present invention provides a compound comprising *Hovenia dulcis* Thunb extract, *Lindera obtusiloba* extract or herbal mixture extract thereof as an effective ingredient.

The composition of the present invention includes an anti-oxidative composition, an anti-fibrosis composition, a liver function improving composition and a kidney function improving composition.

Hereinafter, the present invention is described in detail.

The extracting method for *Hovenia dulcis* Thunb extract, *Lindera obtusiloba* extract or herbal mixture extract thereof of the present invention is as follows.

*Hovenia dulcis* Thunb or *Lindera obtusiloba* is washed with water and then dried in the shadow. The dried *Hovenia dulcis* Thunb or *Lindera obtusiloba* is put in a reflex extractor, to which purified water is added and heated at 100° C. for 90 minutes, leading to hot water extraction. The hot water extract is filtered with a filter paper under reduced pressure when it is still hot. The filtrate is concentrated by using a vacuum evaporator. For long-term storage, the solution is dried by using a freeze dryer. The stems, flowers, leaves and seeds of *Hovenia dulcis* Thunb or *Lindera obtusiloba* are all available in the present invention.

The composition rate of herbs for the composition of the present invention is determined based on the dry weight of each herb. Precisely, *Hovenia dulcis* Thunb and *Lindera obtusiloba* are mixed at the ratio of 3:2~1:1, and more preferably mixed at the ratio of 2:1~1:1. Such ratio is determined under the consideration of effective dosage of each herb and side effects of it, and the pharmaceutical effects are dropped rapidly or side effects might be a problem when the ratio is out of the above range.

GOT, GPT, ALP, BUN and total bilirubin, which are all liver function indices, are all lowered in the group administered with *Hovenia dulcis* Thunb extract, *Lindera obtusiloba* extract or herbal mixture extract thereof, indicating that the extract of the present invention has excellent liver function improving effect. In the meantime, ALP and BUN are not only used as liver function indices but also used as kidney function indices. Thus, the lowered levels of ALP and BUN indicate that *Hovenia dulcis* Thunb extract, *Lindera obtusiloba* extract or herbal mixture extract thereof of the present invention has excellent kidney function improving effect, as well.

*Hovenia dulcis* Thunb extract, *Lindera obtusiloba* extract or herbal mixture extract thereof of the present invention reduces the amount of hydroxyproline in liver tissues but increases that in kidney tissues, indicating that the extract of the invention has excellent anti-fibrosis and kidney protective effects. In particular, the herbal extract extracted from the mixture of *Hovenia dulcis* Thunb and *Lindera obtusiloba* shows higher effects than each individual extract, that is the mixture extract reduces hydroxyproline in liver tissues more but increases it in kidney tissues more than each individual extract.

*Hovenia dulcis* Thunb extract, *Lindera obtusiloba* extract or herbal mixture extract thereof of the present invention can reduce the level of malondialdehyde, an index for lipid peroxidation in liver and kidney tissues, indicating that the extract of the invention has excellent anti-oxidative effect.

Liver cell line and kidney cell line treated with *Hovenia dulcis* Thunb extract, *Lindera obtusiloba* extract or herbal mixture extract thereof of the present invention show high cell viability, indicating that the extract of the present invention has excellent liver cell and kidney cell protective effects.

Therefore, the composition of the present invention can be effectively used for the improvement and the protection of liver and kidney functions and for anti-oxidation and anti-fibrosis as well.

The composition of the present invention can additionally include, in addition to *Hovenia dulcis* Thunb extract, *Lindera obtusiloba* extract or herbal mixture extract thereof, one or more effective ingredients having the same or similar functions to the extract of the present invention.

*Hovenia dulcis* Thunb extract, *Lindera obtusiloba* extract or herbal mixture extract thereof of the present invention can be administered orally or parenterally and be used in general forms of pharmaceutical formulation. The herbal mixture extract of the present invention can be prepared for oral or parenteral administration by mixing with generally used fillers, extenders, binders, wetting agents, disintegrating agents, diluents such as surfactant, or excipients. Solid formulations for oral administration are tablets, pills, dusting powders, granules and capsules. These solid formulations are prepared by mixing one or more suitable excipients such as starch, calcium carbonate, sucrose, lactose, gelatin, etc. Except for the simple excipients, lubricants, for example magnesium stearate, talc, etc, can be used. Liquid formulations for oral administration are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, freeze-drying agent and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The dosage units can contain, for example, 1, 2, 3 or 4 individual doses or ½, ⅓ or ¼ of an individual dose. An individual dose preferably contains the amount of active compound which is administered in one application and which usually corresponds to a whole, ½, ⅓ or ¼ of a daily dose. The effective dosage of *Hovenia dulcis* Thunb extract, *Lindera obtusiloba* extract or herbal mixture extract thereof of the present invention is 200~600 mg/kg, respectively, and more preferably 300~400 mg/kg, and the administration times are 1~6 times a day.

The composition of the present invention can be administered singly or combination with surgical operation, radiotherapy, hormone therapy, chemotherapy and biological reaction regulator, to improve liver and kidney functions and to obtain anti-oxidative and anti-fibrosis effects.

The composition of the present invention can be added in health food to improve liver and kidney functions and to obtain anti-oxidative and anti-fibrosis effects. At this time, *Hovenia dulcis* Thunb extract, *Lindera obtusiloba* extract or herbal mixture extract thereof of the present invention can be added as it is or after being mixed with other food or ingredients, according to the conventional method. The mixing ratio of effective ingredients is determined by the purpose of use (prevention, health or therapeutic treatment). In the case of producing food or beverages containing *Hovenia dulcis* Thunb extract, *Lindera obtusiloba* extract or herbal mixture extract thereof of the present invention, the extract is preferably added by under 15 weight %, more preferably under 10 weight %, to the raw material. However, the content of the extract might be less than the above when it is administered for long-term to improve health conditions but the effective dosage could contain more than the above amount because the extract of the invention is very safe.

There is no limit in applicable food, which is exemplified by meats, sausages, bread, chocolate, candies, snacks, cookies, pizza, ramyun, noodles, gums, dairy products including ice cream, soups, beverages, tea, drinks, alcoholic drinks and vitamin complex, etc, and in fact every health food generally produced are all included.

Health beverages comprising the composition of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. As a sweetener, either natural sweetener such as thaumatin and stevia extract or artificial sweetener such as saccharin and aspartame can be used. The ratio of natural carbohydrate to the composition of the present invention is preferably 0.01~0.04 g to 100 Ml, more preferably 0.02~0.03 g to 100 Ml.

In addition to the ingredients mentioned above, the composition of the present invention can include in variety of nutrients, vitamines, electrolytes, flavoring agents, coloring agents, pectic acid and its salts, arginic acid and its salts, organic acid, protective colloidal viscosifiers, pH regulators, stabilizers, antiseptics, glycerin, alcohols, carbonators which used to be added to soda, etc. The composition of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.01~0.1 weight part per 100 weight part of the composition of the invention.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of *Hovenia Dulcis* Thunb Extract

*Hovenia dulcis* Thunb was washed with water and then dried in the shadow. 20 g of the dried *Hovenia dulcis* Thunb was put in a reflex extractor, to which 1.5 l of purified water was added and was heated at 100° C. for 90 minutes. The hot water extract was filtered with a filter paper under the reduced pressure when it was still hot. The filtrate was concentrated by using a vacuum evaporator. It was dried by a freeze dryer for long-term storage.

The concentrated solution was used for animal test (2 Ml/rat/day).

Example 2

Preparation of *Lindera Obtusiloba* Extract

By using *Lindera obtusiloba*, *Lindera obtusiloba* extract was prepared in analogy to the procedure as described above in example 1.

The concentrated solution was used for animal test (2 Ml/rat/day).

Example 3

Preparation of Herbal Mixture Extract 20 g of dried *Hovenia dulcis* Thunb and 10 g of dried *Lindera obtusiloba* stem were mixed and the extract thereof was prepared in analogy to the procedure as described in example 1.

The concentrated solution was used for animal test (2 Ml/rat/day), and 4-fold concentrated solution was used for MTT and NR assay (50 µl/well).

Experimental Example 1

Anti-Oxidative, Anti-Fibrosis, Liver and Kidney Function Improving and Protective Effects of the Extract in Rats Having Liver and Kidney Damage Induced by Long-Term Administration of Carbon Tetrachloride Experiments were performed as follows in order to investigate anti-oxidative and anti-fibrosis effects as well as liver and kidney function improving and protective effects of *Hovenia dulcis* Thunb extract, *Lindera obtusiloba* extract or herbal mixture extract thereof of the present invention in liver and kidney damage models.

1. Test Animal 12 week old Sprague-Dawley rats weighing about 180~210 g (Damul science, Osan, Korea) were used as test animals. Breeding temperature was 23±2° C. and relative humidity was maintained as 60±10%. Feed (Purina feed) and water were freely given, and day-night cycle was regulated.

The animals were adapted to the test room for 2 weeks, and then divided into 5 groups; ① normal group, ② $CCl_4$ treating group, ③ $CCl_4$+herbal mixture extract treating group, ④ $CCl_4$+*Hovenia dulcis* Thunb extract treating group and ⑤ $CCl_4$+*Lindera obtusiloba* extract treating group. Each group was composed of 10 rats.

2. Inducement of Liver Fibrosis (Cirrhosis) and Kidney Damage

Experimental groups, except the normal group, were administered with olive oil and $CCl_4$ mixture by 1 Ml/rat/day, three times a week for 4 weeks so as to induce liver fibrosis (cirrhosis) and kidney damage.

$CCl_4$ treating group was administered orally with distilled water by 2 Ml/rat/day, $CCl_4$+herbal mixture extract treating group was administered orally with the herbal mixture extract prepared in the above example 3 by 2 Ml/rat/day, $CCl_4$+*Hovenia dulcis* Thunb extract treating group was administered orally with *Hovenia dulcis* Thunb extract prepared in the above example 1 by 2 Ml/rat/day and $CCl_4$+*Lindera obtusiloba* extract treating group was administered orally with *Lindera obtusiloba* extract prepared in the above example 2 also by 2 Ml/rat/day.

Rats in every group including the normal group were weighed, and then anesthetized by ether. Blood was taken from heart by heart puncture, which was left at room temperature for over 2 hours. Then, centrifugation was performed at 3000 rpm for 10 minutes to obtain serum, which was stored at −20° C. The serum was examined to measure the level of GOT, GPT, alkaline phosphatase, BUN and total bilirubin.

Liver and kidney of a rat, which were already damaged by artificial inducement, were extracted and washed with phosphate buffer (pH 7.0), followed by measuring the weight. A part of liver and kidney tissues were kept at −75° C. for the use of measuring hydroxyproline and malondialdehyde (MDA).

Weight changes were measured every week. Ears, tail and feet were investigated to detect the sign of jaundice. The liver was weighed as the rat was sacrificed.

The results were presented by mean±SD, and the significance of difference in averages between control group and experimental group was examined by student's t-test. It was judged as statistically significant when $p<0.005$.

The results are shown in Table 1.

TABLE 1

| | | Liver tissue | | Kidney tissue | |
|---|---|---|---|---|---|
| | Weight (g) | Liver weight (g) | (Liver weight/ body weight) × 100(%) | Kidney weight (g) | (Kidney weight/ body weight) × 100(%) |
| Normal group | 200.8 ± 8.6 | 6.3 ± 0.3 | 3.2 ± 1.3 | 1.23 ± 0.09 | 0.64 ± 0.03 |
| $CCl_4$ treating group | 167.3 ± 19.4 | 12.9 ± 1.9 | 7.7 ± 0.7 | 2.18 ± 0.16 | 0.97 ± 0.17 |
| $CCl_4$ + herbal mixture extract treating group | 190.7 ± 10.3 | 11.7 ± 1.6* | 6.7 ± 0.8* | 1.63 ± 0.10 | 0.86 ± 0.05 |
| $CCl_4$ + *Hovenia dulcis* Thunb extract treating group | 173.2 ± 17.3 | 13.4 ± 1.6 | 7.0 ± 0.6 | 1.57 ± 0.09 | 0.91 ± 0.2* |

TABLE 1-continued

|  | Weight (g) | Liver tissue | | Kidney tissue | |
|---|---|---|---|---|---|
|  |  | Liver weight (g) | (Liver weight/ body weight) × 100(%) | Kidney weight (g) | (Kidney weight/ body weight) × 100(%) |
| $CCl_4$ + Lindera obtusiloba extract treating group | 181.8 ± 16.1 | 12.5 ± 1.2 | 6.9 ± 0.5* | 1.59 ± 0.11 | 0.88 ± 0.07 |

*$p < 0.005$

As shown in Table 1, the changes of the ratio of body weight to liver weight in experimental groups treated with *Hovenia dulcis* Thunb extract, *Lindera obtusiloba* extract and herbal mixture extract thereof of the present invention were not significant, comparing to a control. Likewise, the changes of the ratio of body weight to kidney weight were also insignificant, comparing to a control.

3. Serological and Biochemical Test

1) GOT (AST) Measurement (Using EMBIEL Kit)

500 μl of AST substrate solution was put in two falcon tubes, which were heated at 37° C. for 3~5 minutes. The substrate solution was diluted with standard solution in one tube, and in the other tube, 100 μl of serum sample was added. Reaction was induced in both tubes at 37° C. for 60 minutes. 100 μl of purified water and 500 μl of coloring solution (2,3-dinitrophenylhydrazine) were added to each tube, which were then left at room temperature for 20 minutes. 5 Ml of 0.4 N NaOH was added to each tube, followed by reaction at room temperature for 10 minutes. OD was measured at 505 nm.

2) GPT (ALT) Measurement (Using EMBIEL Kit)

150 μl of ALT substrate solution was put in two falcon tubes, which were heated at 37° C. for 4 minutes. The substrate solution was diluted with standard solution in one tube, and in the other tube, 100 μl of serum sample was added and reaction was induced at 37° C. for 30 minutes in both tubes. 100 μl of purified water and 500 μl of coloring solution (2,3-dinitrophenylhydrazine) were added to each tube, which was left at room temperature for 20 minutes. 1.5 Ml of 0.4 N NaOH was added to each test tube, followed by reaction at room temperature for 10 minutes. OD was measured at 505 nm.

3) ALP (Alkaline Phosphatase) Measurement 2.0 Ml of ALP substrate buffer (sodium-2-phenylphosphate) was put in three test tubes, which were reacted at 37° C. for 3~5 minutes. 50 μl of serum sample, 50 μl of purified water and 50 μg of standard solution were added to test tubes respectively, followed by reaction at 37° C. for 15 minutes. 2.0 Ml of coloring reagent was added to each test tube and then left at room temperature for 10 minutes. OD was measured at 570 nm within 60 minutes.

4) BUN (Blood Urea Nitrogen) Measurement

20 μl of serum sample, 20 μl of purified water and 20 μl of standard solution were put in three test tubes respectively. 2.0 Ml of enzyme solution was added thereto, followed by reaction at 37° C. for 5 minutes. 2.0 Ml of coloring reagent was added to each tube, which was heated at 37° C. for 10 minutes. OD was measured at 580 nm within 60 minutes.

5) Measurement of Total Bilirubin

100 μl of serum sample, 100 μl of purified water and 100 μl of standard solution were put in three test tubes respectively, to which coloring reagent working toward total bilirubin was added by 600 μl per tube. 600 μl of diazo mixture was added to each test tube, which was left at room temperature for 10 minutes. 600 μl of ferring reagent was added to each tube to induce reaction. OD was measured at 600 nm within 2 hours.

The results are shown in Table 2.

TABLE 2

|  | GOT (IU) | GPT (IU) | ALP (KA) | BUN (mg/dl) | Total bilirubin (mg/dl) |
|---|---|---|---|---|---|
| Normal group | 61.78 ± 6.0 | 13.2 ± 1.0 | 63.5 ± 11.2 | 13.6 ± 1.1 | 0.2 ± 0.05 |
| $CCl_4$ treating group | 241.8 ± 43.1 | 145.3 ± 38.1 | 156.9 ± 36.1 | 23.4 ± 2.1 | 1.6 ± 0.92 |
| $CCl_4$ + Herbal mixture extract treating group | 137.6 ± 52.4** | 69.6 ± 47.0* | 137.0 ± 26.0 | 18.04 ± 6.91 | 0.27 ± 0.14 |
| $CCl_4$ + Hovenia dulcis Thunb extract treating group | 165.1 ± 46.4** | 70.9 ± 42.2* | 143.1 ± 37.9 | 18.6 ± 2.1* | 0.7 ± 0.04 |
| $CCl_4$ + Lindera obtusiloba extract treating group | 144.5 ± 5.7** | 74.4 ± 17.6* | 138.2 ± 14.8 | 18.4 ± 3.6 | — |

*$p < 0.05$,
**$p < 0.005$

As shown in Table 2, the levels of GOT, GPT, ALP, BUN and total bilirubin, which are liver function indices, were significantly low in experimental groups treated with *Hovenia dulcis* Thunb extract, *Lindera obtusiloba* extract and herbal mixture extract thereof of the present invention respectively, comparing to a control. In particular, the level of those indices in the group treated with herbal mixture extract was the lowest.

Thus, *Hovenia dulcis* Thunb extract, *Lindera obtusiloba* extract and herbal mixture extract thereof of the present invention were proved to have excellent liver function improving effect.

And, ALP and BUN are the indices not only for the liver function but also for the kidney function, so that the lowered levels of ALP and BUN by the extract of the invention also mean that *Hovenia dulcis* Thunb extract, *Lindera obtusiloba* extract and herbal mixture extract thereof of the present invention have excellent kidney function improving effect as well.

4. Measurement of Hydroxyproline (Hyp)

1) Preparation of Reagents

① Acetate Citrate Buffer 50 g of sodium acetate trihydrate, 37.5 g of trisodium citrate and 5.5 g of citric acid monohydrate were mixed in 395 Ml of isopropanol. And, the total volume of the mixture was adjusted to 1 l by adding distilled water. pH of the mixing solution was also adjusted to 6.0. The final solution was stored at 4° C.

② Chloramine-T Solution 84 mg of chloramine-T was dissolved in 10 Ml of acetate citrate buffer.

③ Ehrlich's Reagents 10 g of p-dimethylaminobenzaldehyde and 11 Ml of 60% perchloric acid were mixed to prepare a storage solution. 3 Ml of the storage solution was mixed with 8.0 Ml of isopropanol, resulting in Ehrlich's reagent. The reagent was prepared right before use, and the storage solution was stored at 4° C. in shading.

2) Measurement of Hydroxyproline 0.2 g of liver (or kidney) tissues which were frozen or freeze-dried (−50° C., 72 hours) were distributed in a 10 Ml glass bottle. 4 Ml of 6 N HCl was put in the bottle, followed by homogenization with a homogenizer. Then, hydrolysis was performed in a dry oven at 110° C. for 10~24 hours, followed by filtering with a Whatmann filter paper. Likewise, standard solution which was diluted with trans-hydroxyproline 6 N HCl at different concentrations of 0, 0.2, 0.4, 0.6, 0.8 and 1.0 µg/50 µl was also hydrolyzed at 110° C. for 12~14 hours. Each sample and standard solution were taken by 50 µl each and completely dried in a glass bottle to eliminate HCl. 1.2 Ml of 50% isopropanol was added to dissolve sediments. 200 µl of chloramine-T solution was added thereto, followed by reaction at room temperature for 10 minutes. Then, 1.2 Ml of Ehrlich's reagent was added. Coloring was induced at 50° C. for 90 minutes, followed by cooling down at room temperature. OD was measured at 558 nm by using a spectrophotometer.

The content of hydroxyproline in liver tissues (or kidney tissues) was measured by the below formula.

$C$ [Hydroxprolone concentration of 0.2 g liver tissue (or kidney tissue)]=[$HA$ ($OD$ of sample)/$SA$ ($OD$ of standard solution diluted with 1.0 µg/50 µl trans-hydroxyproline 6 N HCl)]×80

$C$×5=Hydroxyproline amount/g liver tissue (or kidney tissue)

The results are shown in Table 3.

TABLE 3

| | Hydroxyproline amount (µg/g) | |
|---|---|---|
| | Liver tissue | Kidney tissue |
| Normal group | 997.7 ± 87.8 | 918.2 ± 78.7 |
| CCl$_4$ treating group | 2201.6 ± 16.0 | 825.6 ± 57.6 |
| CCl$_4$ + Herbal mixture extract treating group | 1094.3 ± 186.7 | 870.4 ± 74.3 |
| CCl$_4$ + *Hovenia dulcis* Thunb extract treating group | *5341118.3 ± 255.0* | 850.2 ± 57.6 |
| CCl$_4$ + *Lindera obtusiloba* extract treating group | 1110.1 ± 201.0* | 860.4 ± 69.3 |

*$p < 0.005$

As shown in Table 3, in the case of experimental groups each treated with *Hovenia dulcis* Thunb extract, *Lindera obtusiloba* extract and herbal mixture extract thereof of the present invention, the content of hydroxyproline was lower in liver tissues and higher in kidney tissues, comparing to a control. In particular, in the case of herbal mixture extract treating group, the content of hydroxyproline in liver tissues was significantly low (50.8%), comparing to a control. But the content of hydroxyproline in kidney was 5.5% higher than a control, 3.0% higher than the group treated with *Hovenia dulcis* Thunb extract, and 1.2% higher than the group treated with *Lindera obtusiloba* extract.

Thus, *Hovenia dulcis* Thunb extract, *Lindera obtusiloba* extract and herbal mixture extract thereof of the present invention were confirmed to have excellent anti-fibrosis and kidney protective effects.

5. Measurement of MDA (Malondialdehyde)

Homogenized tissue sample [0.2 g of liver tissues (or kidney tissues) in 1.8 Ml of 1.15% KCl] and 200 µl of diluted standard material (0, 4, 8, 16, 32 nmol/200 µl tetramethoxypropane) were put together in falcon tube. 200 µl of standard solution diluted with sample was mixed with 100 µl of 0.2% SDS, followed by reaction at room temperature for 10 minutes. 750 µl of 20% acetic acid and 750 µl of 0.8% thiobarbiturate were added thereto. The solution was reacted at 95° C. for 30 minutes, then cooled down in ice. Upon completion of cooling down, 2 Ml of n-butanol was added, followed by centrifugation to obtain supernatant. OD of the supernatant was measured at 532 nm by a spectrophotometer.

The contents of MDA in serum and in tissues were measured as follows.

$C$ [Malondialdehyde concentration of 0.2 g of liver tissue (or kidney tissue) (or 200 µl of serum)]= [$HA$ ($OD$ of sample)/$SA$ ($OD$ of standard solution (8 µmol/1.15% KCl 200 µl))×80

$C$×5=Malondialdehyde amount (µmol/Ml)

The results were shown in Table 4.

TABLE 4

| | Malondialdehyde amount (µmol/Ml) | |
|---|---|---|
| | Liver tissue | Kidney tissue |
| Normal group | 89.6 ± 3.7 | 142.3 ± 12.7 |
| CCl$_4$ treating group | 151.3 ± 27.7 | 181.4 ± 24.4 |
| CCl$_4$ + Herbal mixture extract treating group | 105.9 ± 12.9* | 161.7 ± 13.2 |
| CCl$_4$ + *Hovenia dulcis* Thunb extract treating group | 130.7 ± 25.9 | 168.3 ± 19.8 |
| CCl$_4$ + *Lindera obtusiloba* extract treating group | *593121.3 ± 17.6 | 156.6 ± 14.7* |

*$p < 0.05$

As shown in Table 4, in experimental groups each treated with *Hovenia dulcis* Thunb extract, *Lindera obtusiloba* extract and herbal mixture extract thereof of the present invention, the amount of malondialdehyde, an index for lipid peroxidation, was low in liver and kidney tissues, comparing to a control. In particular, in the group treated with herbal mixture extract, the content in liver tissues was significantly low (31.0%) and that in kidney tissues was also very low (13.0%), comparing to a control.

Therefore, *Hovenia dulcis* Thunb extract, *Lindera obtusiloba* extract and herbal mixture extract thereof of the present invention were confirmed to have excellent anti-oxidative and kidney protective effects.

Experimental Example 2

Cytotoxicity Test

The cell lines used in this invention were NCTC clone 1469 (liver cell line) and vero (kidney cell line), which were purchased from Korea Cell Line Bank (KCLB).

5 mg of MTT powder was dissolved in 1 Ml of phosphate buffer, which was stirred well and then filtered by 0.4 μm filter, resulting in MTT storage solution.

4 mg of NR powder was dissolved in 1 Ml of tertially distilled water, which was then stirred well and filtered by 0.4 μm filter, resulting in NR storage solution.

Trypsin-EDTA containing 0.5% trypsin and 5.3 mM EDTA was purchased and 10-fold diluted with PBS before use.

1) MTT [3-(4,5-Dimethylthiazol-2-yl)-2,5-diphenyl tetrazolium bromide] assay

After removing medium, 1 Ml of trypsin-EDTA solution was added, which was left for 10~20 minutes. Cells were isolated from the vessel and then transferred to 15 Ml falcon tube. 1 Ml of medium was added to culture flask and shacked to isolate all the remaining cells, which were also put in the falcon tube. 10 μl of cell suspension was put in hemocytometer and then cells were counted ($2.5 \times 10^4$ cell/Ml). Cells were inoculated to 96 well plate by 50 μl ($1$~$2 \times 10^5$ cells)/well, to which 150 μl of medium (DMEM+10% FBS+antibiotics) was added. The cells were cultured in a 37° C., 5% $CO_2$ incubator for 24 hours, resulting in cell adhesion.

24 hours later, medium was carefully removed from the cells adhered onto the 96 well plate (Careful attention is required for the medium not to be stained with cells and contaminated). 150 μl of medium was supplemented with 50 μl of *Hovenia dulcis* Thunb extract prepared in example 1, 50 μl of *Lindera obtusiloba* extract prepared in example 2 and 50 μl of herbal mixture extract prepared in example 3, making total volume 200 μl. The solution was cultured in a 37° C., 5% $CO_2$ incubator for 24 hours. At this time, the extract should be added later, otherwise cells are damaged. So, medium should be added first and then the extract was put therein. Upon culturing, the 96 well plate was taken to remove medium. 50 μl/Ml of MTT dye (50 μl of storage solution+950 μl of medium) was added to dilute the solution, which was distributed in each well by 50 μl, followed by further culture in a $CO_2$ incubator for 4 hours. After eliminating supernatant, 100 μl of DMSO was added, followed by stirring for 10 minutes. OD was measured at 540 nm with ELISA reader.

Only medium was added to a control, and viability was investigated.

2) NR (Neutral Red: 3-amino-7-dimethylamino-2-methyl phenazine) assay

After removing medium, 1 Ml of trypsin-EDTA solution was added, which was left for 10~20 minutes. Cells were isolated from the vessel and then transferred to 15 Ml falcon tube. 1 Ml of medium was added to culture flask and shaked to isolate all the remaining cells, which were also put in the falcon tube. 10 μl of cell suspension was put in hemocytometer and then cells were counted ($2.5 \times 10^4$ cell/Ml). Cells were inoculated to 96 well plate by 50 μl ($1$~$2 \times 10^5$ cells)/well, to which 150 μl of medium (DMEM+10% FBS+antibiotics) was added. The cells were cultured in a 37° C., 5% $CO_2$ incubator for 24 hours, resulting in cell adhesion.

24 hours later, medium was carefully removed from the cells adhered onto the 96 well plate (Careful attention is required for the medium not to be stained with cells and contaminated). 150 μl of medium was supplemented with 50 μl of *Hovenia dulcis* Thunb extract prepared in example 1, 50 μl of *Lindera obtusiloba* extract prepared in example 2 and 50 μl of herbal mixture extract prepared in example 3, making total volume 200 μl. The solution was cultured in a 37° C., 5% $CO_2$ incubator for 24 hours. At this time, the extract should be added later, otherwise cells are damaged. So, medium should be added first and then the extract was put therein.

Upon culturing, the 96 well plate was taken to remove medium. 10 μl/Ml of NR dye (10 μl of storage solution+990 μl of medium) was added to dilute the solution, which was distributed in each well by 200 μl, followed by further culture in a 37° C., 5% $CO_2$ incubator for 3 hours. After eliminating the medium, the plate was washed with 100 μl of 1% $CaCl_2$ and 0.5% formaldehyde. Supernatant was removed. Then, 200 μl of 1% acetic acid and 50% ethanol was added, followed by stirring for 10 minutes. OD was measured at 540 nm with ELISA reader.

Only medium was added to a control, and viability was investigated.

The results were shown in Table 5.

TABLE 5

| | Liver cell line (NCTC) | | Kidney cell line (Vero) | |
|---|---|---|---|---|
| | MTT (%) | NR (%) | MTT (%) | NR (%) |
| Herbal mixture extract (*Hovenia dulcis* Thunb + *Lindera obtusiloba*) | 105.70 ± 12.9 | 109.00 ± 5.3 | 96.20 ± 4 | 106.90 ± 7.4 |

TABLE 5-continued

| | Liver cell line (NCTC) | | Kidney cell line (Vero) | |
|---|---|---|---|---|
| | MTT (%) | NR (%) | MTT (%) | NR (%) |
| *Hovenia dulcis* Thunb extract | 44.60 ± 6.6 | 42.30 ± 4.1 | 98.40 ± 4.1 | 99.00 ± 12 |
| *Lindera obtusiloba* extract | 95.7 ± 10.9 | 96.7 ± 5.7 | 98.7 ± 3.8 | 97.3 ± 3.5 |

As shown in Table 5, *Lindera obtusiloba* extract and herbal mixture extract of the present invention showed high cell viability in liver cell line. In particular, herbal mixture extract is more effective to increase cell viability in liver cell line than *Hovenia dulcis* Thunb extract. In the meantime, *Hovenia dulcis* Thunb extract, *Lindera obtusiloba* extract and herbal mixture extract thereof of the present invention did not harm cell viability in kidney cell line.

Therefore, *Hovenia dulcis* Thunb extract, *Lindera obtusiloba* extract and herbal mixture extract thereof of the present invention were confirmed to have excellent liver and kidney protective effects.

Preparative examples of the composition of the present invention are described hereinafter.

Pharmaceutical compositions comprising *Hovenia dulcis* Thunb extract, *Lindera obtusiloba* extract or herbal mixture extract thereof of the present invention were prepared as follows.

Preparative Example 1

Preparation of Pharmaceutical Compositions

1. Preparation of Powders

| | |
|---|---|
| *Hovenia dulcis* Thunb extract (or *Lindera obtusiloba* extract or herbal mixture extract thereof) | 2 g |
| Lactose | 1 g |

The above-mentioned ingredients were mixed together, and airtight bag was filled with the mixture to prepare powders.

2. Preparation of Tablets

| | |
|---|---|
| *Hovenia dulcis* Thunb extract (or *Lindera obtusiloba* extract or herbal mixture extract thereof) | 100 mg |
| Corn starch | 100 mg |
| Lactose | 100 mg |
| Magnesium stearate | 2 mg |

The above-mentioned ingredients were mixed together, and tablets were prepared by tabletting according to the conventional tablet producing method.

3. Preparation of Capsules

| | |
|---|---|
| *Hovenia dulcis* Thunb extract (or *Lindera obtusiloba* extract or herbal mixture extract thereof) | 100 mg |
| Corn starch | 100 mg |
| Lactose | 100 mg |
| Magnesium stearate | 2 mg |

The above-mentioned ingredients were mixed together, and gelatin capsules were filled with the mixture to prepare capsules according to the conventional capsule producing method.

Preparative Example 2

Preparation of Food

Food comprising *Hovenia dulcis* Thunb extract, *Lindera obtusiloba* extract or herbal mixture extract thereof of the present invention was prepared as follows.

1. Preparation of Spices and Condiments

Spices and condiments for health improvement that contains *Hovenia dulcis* Thunb extract (or *Lindera obtusiloba* extract or herbal mixture extract thereof) of the present invention by 20~95 weight % were prepared.

2. Preparation of Tomato Ketchup and Source

Tomato ketchup or source for health improvement was prepared by adding *Hovenia dulcis* Thunb extract (or *Lindera obtusiloba* extract or herbal mixture extract thereof) of the present invention by 0.2~1.0 weight % to tomato ketchup or source.

3. Preparation of Flour Foods

*Hovenia dulcis* Thunb extract (or *Lindera obtusiloba* extract or herbal mixture extract thereof) of the present invention was added to flour by 0.5~5.0 weight %, and the mixture was used to prepare bread, cake, cookies, cracker and noodles to produce health improving foods.

4. Preparation of Soups and Gravies

Health improving processed meat, noodle soups and gravies were prepared by adding *Hovenia dulcis* Thunb extract (or *Lindera obtusiloba* extract or herbal mixture extract thereof) of the present invention by 0.1~5.0 weight % to soups and gravies.

5. Preparation of Ground Beef

Health improving ground beef was prepared by adding *Hovenia dulcis* Thunb extract (or *Lindera obtusiloba* extract or herbal mixture extract thereof) of the present invention by 10 weight % to ground beef.

6. Preparation of Dairy Products

*Hovenia dulcis* Thunb extract (or *Lindera obtusiloba* extract or herbal mixture extract thereof) of the present invention was added to milk by 5~10 weight %, which was then used for the production of health improving dairy products including butter and ice cream.

7. Preparation of Cerial

Brown rice, barley, glutinous rice and Job's tears were gelatinized, dried and roasted by the conventional method, followed by pulverization with a pulverizer, resulting in 60-mesh granules.

Black bean, black sesame, *Perilla japonica* were steamed, dried and roasted by the conventional method, followed by pulverization with a pulverizer, resulting in 60-mesh granules.

*Hovenia dulcis* Thunb extract (or *Lindera obtusiloba* extract or herbal mixture extract thereof) of the present invention was concentrated under reduced pressure in a vacuum concentrator, and then dried by spray dryer. The dried product was pulverized into 60-mesh granules.

Crops, seeds and the dried powder of *Hovenia dulcis* Thunb extract (or *Lindera obtusiloba* extract or herbal mixture extract thereof) were mixed by the following ratio.

Crops (brown rice 30 weight %, job's tears 15 weight %, barley 20 weight %),

Seeds (*Perilla japonica* 7 weight %, black bean 8 weight %, black sesame 7 weight %), Dried powder of *Hovenia dulcis* Thunb extract (or *Lindera obtusiloba* extract or herbal mixture extract thereof) (3 weight %),

*Ganoderma lucidum* (0.5 weight %),

*Rehmannia glutinosa* (0.5 weight %)

Preparative Example 3

Preparation of Beverages

1. Preparation of Carbonated Beverage

Sugar (5~10%), citric acid (0.05~0.3%), caramel (0.005~0.02%) and vitamin C (0.1~1%) were mixed together, to which purified water (79~94%) was added, resulting in syrup. The syrup was sterilized at 85~98° C. for 20~180 seconds, then mixed with cooling water at the ratio of 1:4. Carbon dioxide was injected by 0.5~0.82% thereto, resulting in the preparation of carbonated beverage comprising *Hovenia dulcis* Thunb extract (or *Lindera obtusiloba* extract or herbal mixture extract thereof) of the present invention.

2. Preparation of Health Beverage

Optional ingredients such as liquid fructose (0.5%), oligosaccharide (2%), sugar (2%), salt (0.5%), water (75%) and *Hovenia dulcis* Thunb extract (or *Lindera obtusiloba* extract or herbal mixture extract thereof) were mixed evenly. After pasteurization, the mixture was put in small container such as pet or glass bottle, resulting in the preparation of health beverages.

3. Preparation of Vegetable Juice 5 g of *Hovenia dulcis* Thunb extract (or *Lindera obtusiloba* extract or herbal mixture extract thereof) of the present invention was added to 1,000 Ml of tomato or carrot juice to prepare health improving vegetable juice.

4. Preparation of Fruit Juice 1 g of *Hovenia dulcis* Thunb extract (or *Lindera obtusiloba* extract or herbal mixture extract thereof) of the present invention was added to 1,000 Ml of apple or grape juice to prepare health improving fruit juice.

INDUSTRIAL APPLICABILITY

*Hovenia dulcis* Thunb extract, *Lindera obtusiloba* extract or herbal mixture extract thereof of the present invention is highly effective for the improvement of liver functions since it can lower the level of GOT, GPT, ALP, BUN and total bilirubin, which are major liver function indices. ALP and BUN are also used as kidney function indices, so the decrease of the level of ALP and BUN by the extract of the present invention indicates that *Hovenia dulcis* Thunb extract, *Lindera obtusiloba* extract or herbal mixture extract thereof of the invention can improve kidney functions as well.

*Hovenia dulcis* Thunb extract, *Lindera obtusiloba* extract or herbal mixture extract thereof of the present invention also can lower the amount of hydroxyproline in liver but increase the amount of hydroxyproline in kidney, suggesting that the extract above has excellent anti-fibrosis and kidney protecting effects.

In addition, *Hovenia dulcis* Thunb extract, *Lindera obtusiloba* extract or herbal mixture extract thereof of the present invention can lower the level of malondialdehyde, an index of lipid peroxidation in liver and kidney tissues, suggesting that the extract has excellent anti-oxidative effect.

*Hovenia dulcis* Thunb extract, *Lindera obtusiloba* extract or herbal mixture extract thereof of the present invention promotes cell viability in liver and kidney cell lines, indicating that the extract has excellent liver and kidney cell protective effects.

Therefore, the composition of the present invention can be effectively used not only for anti-oxidation and anti-fibrosis but also for the protection and the improvement of liver and kidney functions.

We claim:

1. A method for treating fibrosis in a subject in need thereof comprising administering a pharmaceutically effective amount of an extract of *Hovenia dulcis* Thunb and *Lindera obtusiloba* to the subject, wherein the *Hovenia dulcis* Thunb and *Lindera obtusiloba* are mixed at the ratio of 2:1~1:1, weight:weight.

2. A method for improving kidney function in a subject in need thereof comprising administering a pharmaceutically effective amount of an extract of *Hovenia dulcis* Thunb and *Lindera obtusiloba* to the subject, wherein the *Hovenia dulcis* Thunb and *Lindera obtusiloba* are mixed at the ratio of 2:1~1:1, weight:weight.

* * * * *